US012746287B2

(12) United States Patent
Mittur

(10) Patent No.: US 12,746,287 B2
(45) Date of Patent: Sep. 29, 2026

(54) METHODS FOR INCREASING THE BIOAVAILABILITY OF NUCLEOSIDE MEDICINAL AGENTS

(71) Applicant: UCB BIOSCIENCES, INC., Morrisville, NC (US)

(72) Inventor: Aravind Mittur, Emeryville, CA (US)

(73) Assignee: UCB BIOSCIENCES, INC., Morrisville, NC (US)

( * ) Notice: Subject to any disclaimer, the term of this patent is extended or adjusted under 35 U.S.C. 154(b) by 439 days.

(21) Appl. No.: 18/351,154

(22) Filed: Jul. 12, 2023

(65) Prior Publication Data

US 2024/0016938 A1 Jan. 18, 2024

Related U.S. Application Data

(60) Provisional application No. 63/388,470, filed on Jul. 12, 2022.

(51) Int. Cl.
*A61K 47/26* (2006.01)
*A61K 9/00* (2006.01)

(52) U.S. Cl.
CPC ............ *A61K 47/26* (2013.01); *A61K 9/0053* (2013.01)

(58) Field of Classification Search
CPC .............................. A61K 47/26; A61K 9/0053
See application file for complete search history.

(56) References Cited

U.S. PATENT DOCUMENTS

| | | | | |
|---|---|---|---|---|
| 5,681,581 | A * | 10/1997 | Dunn ................. | A61K 31/7072 424/490 |
| 10,292,996 | B2 | 5/2019 | Hirano et al. | |
| 10,471,087 | B2 | 11/2019 | Hirano et al. | |
| 11,337,980 | B2 | 5/2022 | Seves et al. | |
| 11,628,182 | B2 | 4/2023 | Dipietro | |
| 11,649,259 | B2 | 5/2023 | Glidden | |
| 2021/0100917 | A1 | 4/2021 | Hirano et al. | |
| 2021/0244754 | A1* | 8/2021 | Hirano ................. | A61K 31/708 |
| 2022/0096514 | A1 | 3/2022 | Quan | |
| 2023/0000890 | A1 | 1/2023 | Dipietro | |

OTHER PUBLICATIONS

Koziolek, Mirko, et al. "The mechanisms of pharmacokinetic food-drug interactions—A perspective from the UNGAP group." European Journal of Pharmaceutical Sciences 134 (2019): 31-59. (Year: 2019).*

Hermann, Robert, et al. "Cladribine as a potential object of nucleoside transporter-based drug interactions." Clinical Pharmacokinetics 61.2 (2022, published online Dec. 11, 2021): 167-187. (Year: 2022).*

Deng, J., et al., "A Review of Food-Drug Interactions on Oral Drug Absorption," Drugs 77:1833-1855, Springer Nature, Germany (2017).

Gezmen-Karada, M., et al., "Role of food-drug interactions in neurological and psychological diseases," Acta Neurobiol. Exp. 78:187-197, Nencki Institute of Experimental Biology, Poland (2018).

Hernandez-Voth, A., et al., "Deoxynucleoside therapy for respiratory involvement in adult patients with thymidine kinase 2-deficient myopathy," BMJ Open Respir. Res. 7:e000774, BMJ, United Kingdom (2020).

International Search Report and Written Opinion for International Application No. PCT/US2023/027508, International Search Authority, United States, mailed on Oct. 12, 2023, 10 pages.

Tinker, R.J., et al., "Current and Emerging Clinical Treatment in Mitochondrial Disease," Mol. Diagn. Ther. 25:181-206, Springer Nature, Germany (2021).

Blazquez-Bermejo, C., et al., "Age-related metabolic changes limit efficacy of deoxynucleoside-based therapy in thymidine kinase 2-deficient mice," EBioMedicine 46:342-355, Elsevier, Netherlands (Jul. 2019).

Dimauro, S., and Schon, E.A., "Mitochondrial respiratory-chain diseases," N. Engl. J. Med. 348(26):2656-2668, Massachusetts Medical Society, United States (Jun. 2003).

Dimauro, S., and Hirano, M., "Mitochondrial encephalomyopathies: an update," Neuromuscul. Disord. 15(4):276-286, Elsevier, Netherlands (Apr. 2005).

Dominguez-Gonzalez, C., et al., "Late-onset thymidine kinase 2 deficiency: a review of 18 cases," Orphanet J. Rare Dis. 14(1):100, BMC, United Kingdom (May 2019).

Garone, C., et al., "Retrospective natural history of thymidine kinase 2 deficiency," J. Med. Genet. 55(8):515-521, BMJ Publishing Group, United Kingdom (Mar. 2018).

Hirano, M., et al., "Defects of intergenomic communication: autosomal disorders that cause multiple deletions and depletion of mitochondrial DNA," Semin. Cell Dev. Biol. 12(6):417-427, Elsevier, Netherlands (Dec. 2001).

Hirano, M., et al., "Emerging therapies for mitochondrial diseases," Essays Biochem. 62(3):467-481, Portland Press, United Kingdom (Jul. 2018).

Lopez-Gomez, C., et al., "Deoxycytidine and deoxythymidine treatment for thymidine kinase 2 deficiency," Ann. Neurol. 81(5):641-652, Wiley, United States (May 2017).

Lopez-Gomez, C., et al., "Bioavailability and cytosolic kinases modulate response to deoxynucleoside therapy in TK2 deficiency," EBioMedicine 46:356-367, Elsevier, Netherlands (Aug. 2019).

Rangaraj, N., et al., "Fast-Fed Variability: Insights into Drug Delivery, Molecular Manifestations, and Regulatory Aspects," Pharmaceutics 14(9):1807, MDPI, Switzerland (Aug. 2022).

Saada, A., et al., "Mutant mitochondrial thymidine kinase in mitochondrial DNA depletion myopathy," Nat. Genet. 29(3): 342-344, Nature Publishing Group, United Kingdom (Oct. 2001).

Wang, J., et al., "TK2-Related Mitochondrial DNA Maintenance Defect, Myopathic Form," *GeneReviews*® [Internet]. Seattle (WA): University of Washington, United States (Dec. 2012).

* cited by examiner

*Primary Examiner* — Scarlett Y Goon
*Assistant Examiner* — David H Cho
(74) *Attorney, Agent, or Firm* — Sterne, Kessler, Goldstein & Fox P.L.L.C.

(57) ABSTRACT

Provided are methods for increasing the bioavailability of nucleoside medicinal agents in treating mitochondrial depletion syndromes. In particular, the methods relate to increasing the bioavailability of deoxycytidine and deoxythymidine by administering a therapeutically effective amount of deoxycytidine and deoxythymidine with food.

23 Claims, 6 Drawing Sheets

Subject 5101 only has one concentration value for Treatment A, and therefore, was excluded from mean figure.
dT = Deoxythymidine; LLOQ = 0.5

METHODS FOR INCREASING THE BIOAVAILABILITY OF NUCLEOSIDE MEDICINAL AGENTS

CROSS REFERENCE TO RELATED APPLICATIONS

This application claims priority to U.S. Provisional Patent Application No. 63/388,470, filed Jul. 12, 2022, which is incorporated herein by reference in its entirety.

FIELD OF THE INVENTION

The invention relates to the field of mitochondrial diseases. In some aspects, the invention is directed to methods for increasing the bioavailability of nucleoside medicinal agents, deoxycytidine and deoxythymidine, in treating mitochondrial depletion syndromes.

BACKGROUND OF THE DISCLOSURE

Mitochondrial diseases are clinically heterogeneous diseases due to defects of the mitochondrial respiratory chain (RC) and oxidative phosphorylation, the biochemical pathways that convert energy in electrons into adenosine triphosphate (ATP). The respiratory chain is comprised of four multi-subunit enzymes (complexes I-IV) that transfer electrons to generate a proton gradient across the inner membrane of mitochondria and the flow of protons through complex V drives ATP synthesis (DiMauro and Schon 2003; DiMauro and Hirano 2005). Coenzyme Q10 (CoQ10) is an essential molecule that shuttles electrons from complexes I and II to complex III. The respiratory chain is unique in eukaryotic, e.g., mammalian, cells by virtue of being controlled by two genomes, mitochondrial DNA (mtDNA) and nuclear DNA (nDNA). As a consequence, mutations in either genome can cause mitochondrial diseases. Most mitochondrial diseases affect multiple body organs and have very high mortality rates in the most severely afflicted patients and, in early onset patients, a rapidly progressive course of disease. There are no approved treatments for mitochondrial diseases, only supportive therapies, such as the administration of CoQ10 and its analogs to enhance respiratory chain activity and to detoxify reactive oxygen species (ROS) that are toxic by-products of dysfunctional respiratory chain enzymes.

Mitochondrial diseases can be categorized as mitochondrial depletion syndromes and mitochondrial DNA deletion syndromes. In some mitochondrial diseases both mtDNA depletion and deletions can occur.

Mitochondrial DNA depletion syndromes (MDS) are a clinically and genetically heterogeneous group of clinically distinct syndromes that are typically recessively inherited diseases with early or juvenile onset and characterized by a severe reduction of mtDNA content.

Mitochondrial DNA deletion syndromes are most often caused by spontaneous (de novo) gene deletions and are not inherited, however, de novo mutations in nuclear genes involved in mitochondrial DNA replication also cause mtDNA deletions.

Both depletion and deletion syndromes result in low mitochondrial energy production with symptoms manifesting in high energy requirement organs and tissues such as the brain, liver and muscle. Based on affected tissues and the mtDNA content of those tissues, the clinical presentations of MDS can be classified into three main phenotypic forms: encephalomyopathic, myopathic and hepatocerebral.

MDS is a frequent cause of severe childhood encephalomyopathy characterized by reduction of mitochondrial DNA (mtDNA) copy number in tissues and insufficient synthesis of mitochondrial RC complexes (Hirano, et al. 2001). The mitochondrial genome contains 37 genes that encode for two rRNAs, 22 tRNAs, and 13 protein subunits, all are involved in the oxidative phosphorylation process that acts as the "powerhouse" of animal and plant cells.

In contrast, much of the replication and maintenance proteins involved in keeping adequate levels of functional mtDNA is encoded in nuclear DNA. Nuclear genes that function in mitochondrial maintenance of nucleotide pools needed for DNA synthesis are, by way of non-limiting example, TK2, SUCLA2, SUCLG1, RRM2B, DGUOK, and TYMP, and those that function in mtDNA replication are, by way of non-limiting example, POLG and C10orf2. One gene, for example, is thymidine kinase 2 (TK2), a nuclear gene product. TK2 deficiency (TK2d) is caused by an autosomal recessive genetic defect in the thymidine kinase 2 gene and results in an ultra-rare mitochondrial DNA depletion and deletions syndrome. [Domínguez-González C, et al. *Orphanet J Rare Dis.* 2019; 14(1):100; Hirano M, et al. *Essays Biochem.* 2018; 62(3):467-481.]

Normally, the expression product of TK2 translation is localized into mitochondria where this protein catalyzes the phosphorylation of deoxythymidine and, to some extent, deoxycytidine to form the respective monophosphates. [Saada A, et al. *Nat Genet.* 2001; 29(3):342-344.] Mutations in this gene therefore impair the availability of these monophosphate precursors to form the ultimate deoxyribonucleotide triphosphate (dNTP) components necessary for mtDNA replication.

The clinical presentation of TK2d is characterized by progressive proximal muscle weakness, respiratory insufficiency, and premature death in most patients. [Garone 2018 natl hx/p2para5; Wang 2018 natl hx/p5para3-4] TK2d patients and their caregivers, report that mobility, respiratory function, and hospitalizations are the most substantial health-related impacts, and that fatigue has the most substantial impact on quality of life. [Jensen M P, et al. Poster presented at World Muscle Society meeting, Sep. 20-24, 2021]. There are at present no disease-specific therapies with regulatory approval and treatment is therefore supportive or experimental.

Reports on the use of chemical-grade pyrimidine deoxynucleotides (i.e., non-GMP grade (not manufactured under Current Good Manufacturing Practices)), and later, deoxynucleosides under compassionate use protocols to treat patients with TK2d have been published. [Dominguez-Gonzilez C, et al. *Orphanet J Rare Dis.* 2019; 14(1):100.] Initially, patients were treated with deoxynucleotides deoxythymidine monophosphate and deoxycytidine monophosphate (dCMP/dTMP) in an effort to by-pass the defective TK2 enzyme and supplement mitochondria with deoxythymidine monophosphate and deoxycytidine monophosphate directly. See, for example, U.S. Pat. No. 10,292,996. Later, unexpectedly better results were obtained with the deoxynucleoside combination of deoxycytidine and deoxythymidine. See, for example, U.S. Pat. No. 10,471,087, which describes the treatment of TK2 deficiency with these pyrimidine nucleosides. The combined nucleoside administration is important, as unbalanced nucleoside pools can lead to loss of fidelity in mtDNA replication, possibly introducing deleterious mutations.

An investigative product under development referred to as MT1621 is a combination of deoxycytidine and deoxythymidine. MT1621 is a fixed-dose drug product including equal weights of dC and dT (hereafter, "fixed-dose product") and formulated as a powder for oral administration by reconstitution in water or juice. MT1621 provides nucleoside therapy of equal weight ratios of dC and dT to restore the dNTP pool by two mechanisms. [Blázquez-Bermejo C, et al. Age-related metabolic changes limit efficacy of deoxynucleoside-based therapy in thymidine kinase 2-deficient mice. *EBioMedicine.* 2019; 46:342-355; Lopez-Gomez C, et al. Deoxycytidine and Deoxythymidine Treatment for Thymidine Kinase 2 Deficiency. *Annals of Neurology.* 2017; 81(5):641-652, Lopez-Gomez C, et al. Bioavailability and cytosolic kinases modulate response to deoxynucleoside therapy in TK2 deficiency. *EBioMedicine.* 2019; 46:356-367.] The first mechanism is addition of nucleoside supplementation to maximize residual TK2 activity in the mitochondria and restore mtDNA replication. Second, MT1621 utilizes the thymidine kinase 1 (TK1)/deoxycytidine kinase (dCK) salvage pathway in the cytosol to restore dNTP pools. Exogenous dT and dC drive formation of the deoxynucleotides dCMP and dTMP via TK1/dCK-mediated phosphorylation of dT and dC, which can enter mitochondria via membrane transporters, thus restoring mtDNA replication by a mechanism that bypasses the TK2 enzyme.

Nucleoside supplementation treatment presents challenges to many TK2d patients in that the multi-gram quantities of nucleosides required to be dosed each day is not always possible since providing sufficient doses of the nucleosides can be limited by dose limiting side effects that can occur, such as diarrhea and gastrointestinal upset. One strategy to avoid the side effects has been to dose three times per day with consequently lower amounts at each dose. There remains a need for improved dosing, e.g., to reduce side effects.

SUMMARY OF THE DISCLOSURE

Certain aspects of the invention described herein provides an improved method of increasing drug absorption and reducing dose-limiting side effects.

In some aspects, the disclosure provides a method of reducing the dosing volume of deoxycytidine (dC) and deoxythymidine (dT).

In some aspects, the disclosure provides a method of increasing absorption and tolerability of deoxycytidine (dC) and deoxythymidine (dT) by providing a patient with dC or dT or both nucleosides, along with instructions to patient to ingest the drug combination shortly before, during, or shortly after a meal.

Structures of 2'-deoxycytidine (β-D-2'-deoxycytidine) and 2'-deoxythymidine (β-D-2'-deoxythymidine) are shown below. Endogenous nucleosides (such as (β-D-2'-deoxycytidine) are referred to as canonical nucleosides and they have the same molecular formula and opposite stereochemical structure as non-endogenous nucleosides (such as (β-L-2'-deoxycytidine).

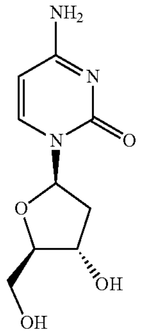

dC

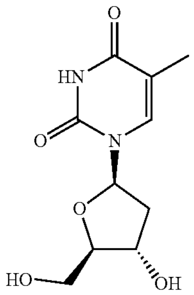

dT

DETAILED DESCRIPTION OF THE INVENTION

Figure 1:
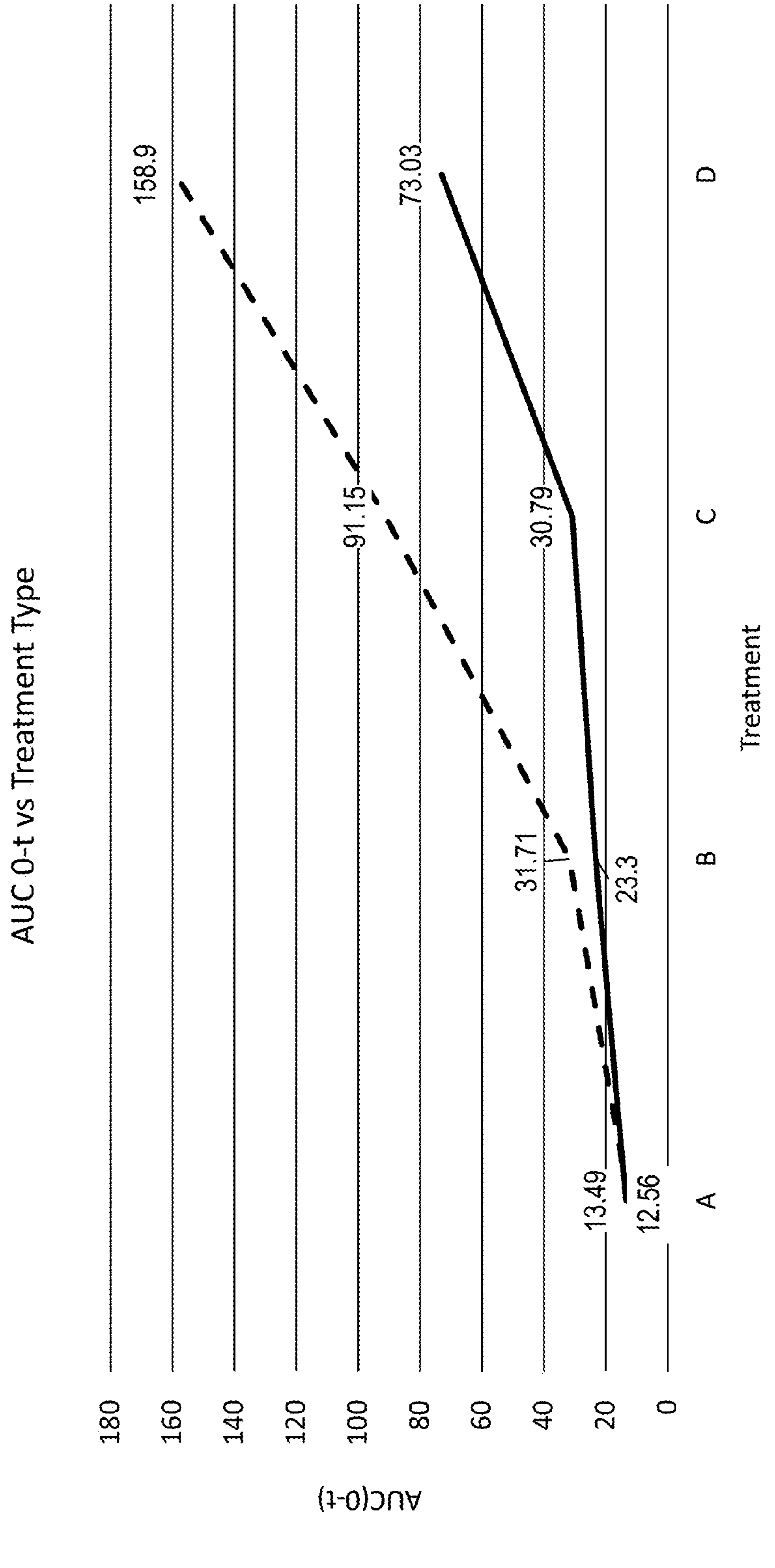
FIG. 1 shows a plot of extent of absorption (measured as AUC0-t) of dT and dC for the four treatment regimens described herein (see also Table 2). Dashed line=deoxythymidine (ng*h/mL) exposure; solid line=deoxycytidine exposure (ng*h/mL) for each treatment group.
Figure 2:
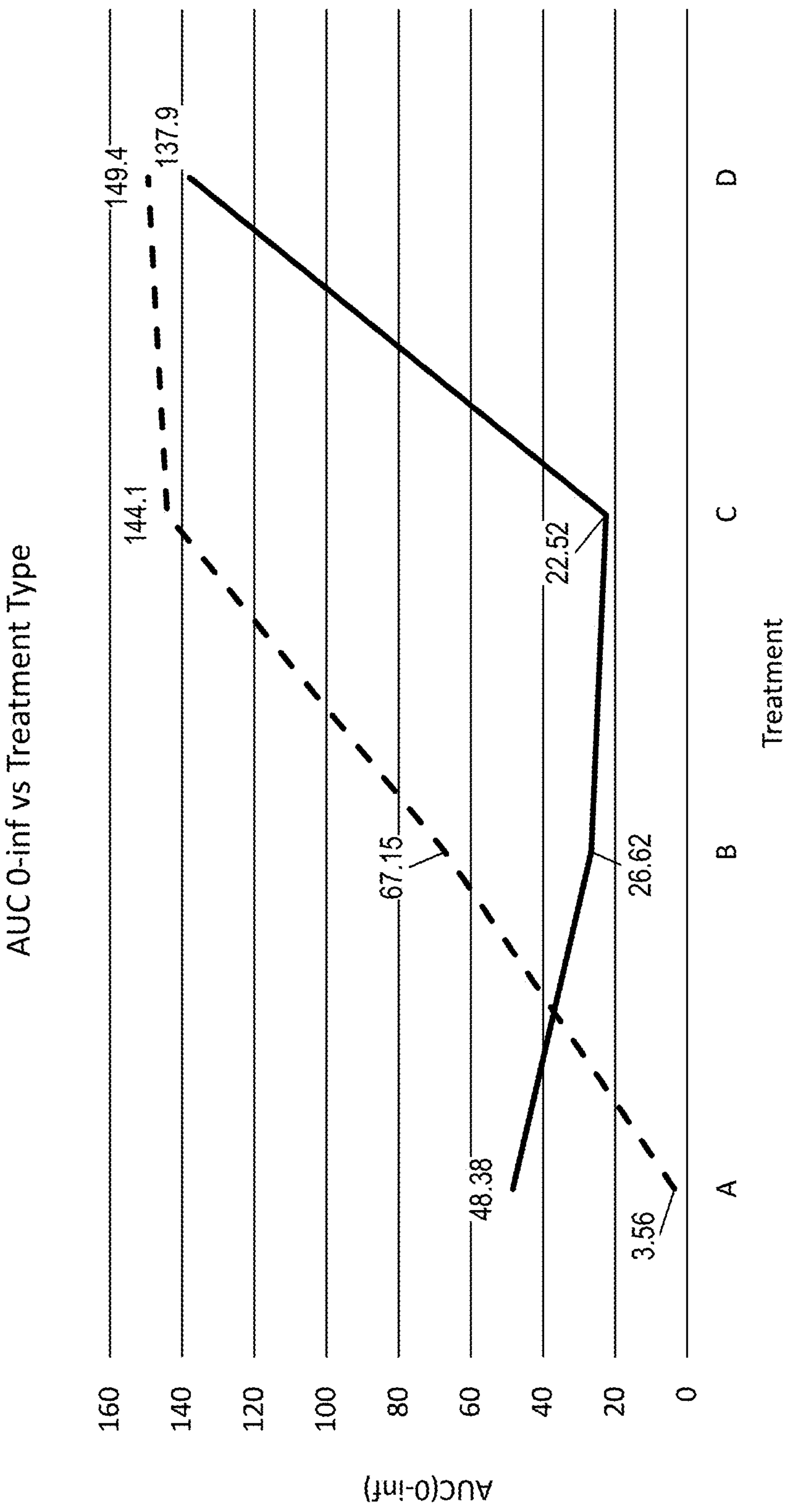
FIG. 2 shows a plot of extent of absorption (measured as AUC0-inf) of dT and dC for the four treatment regimens described herein (see also Table 3). Dashed line=deoxythymidine (ng*h/mL) exposure; solid line=deoxycytidine exposure (ng*h/mL) for each treatment group.
Figure 3:
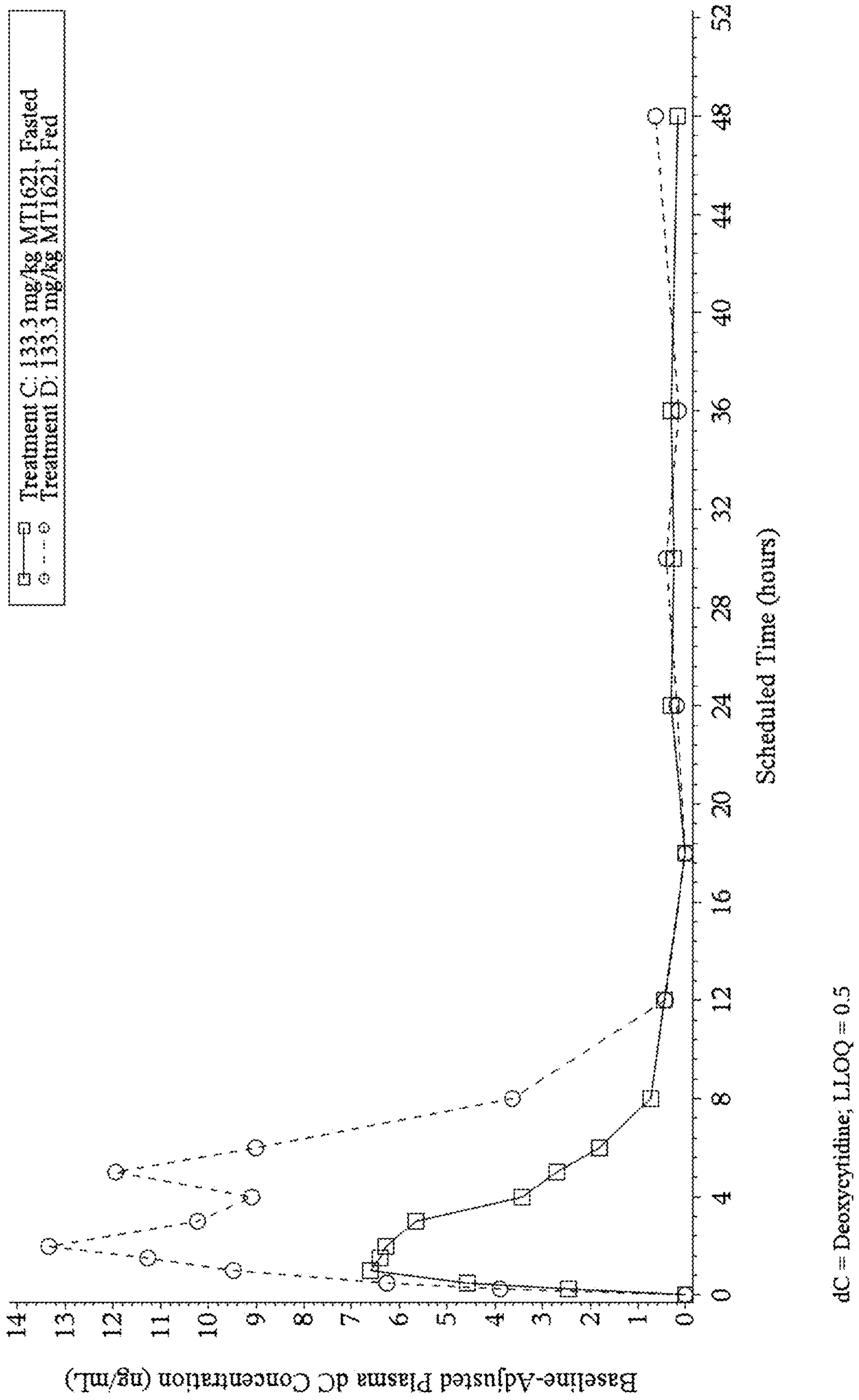
FIG. 3 shows a plot of baseline-adjusted arithmetic mean plasma dC concentration-time profiles following the administration of a single dose of 133.3 mg/kg MT1621 (i.e., 133.3 mg/kg of dC and 133.3 mg/kg of dT), Fasted or 133.3 mg/kg MT1621 (i.e., 133.3 mg/kg of dC and 133.3 mg/kg of dT), Fed in linear scale.
Figure 4:
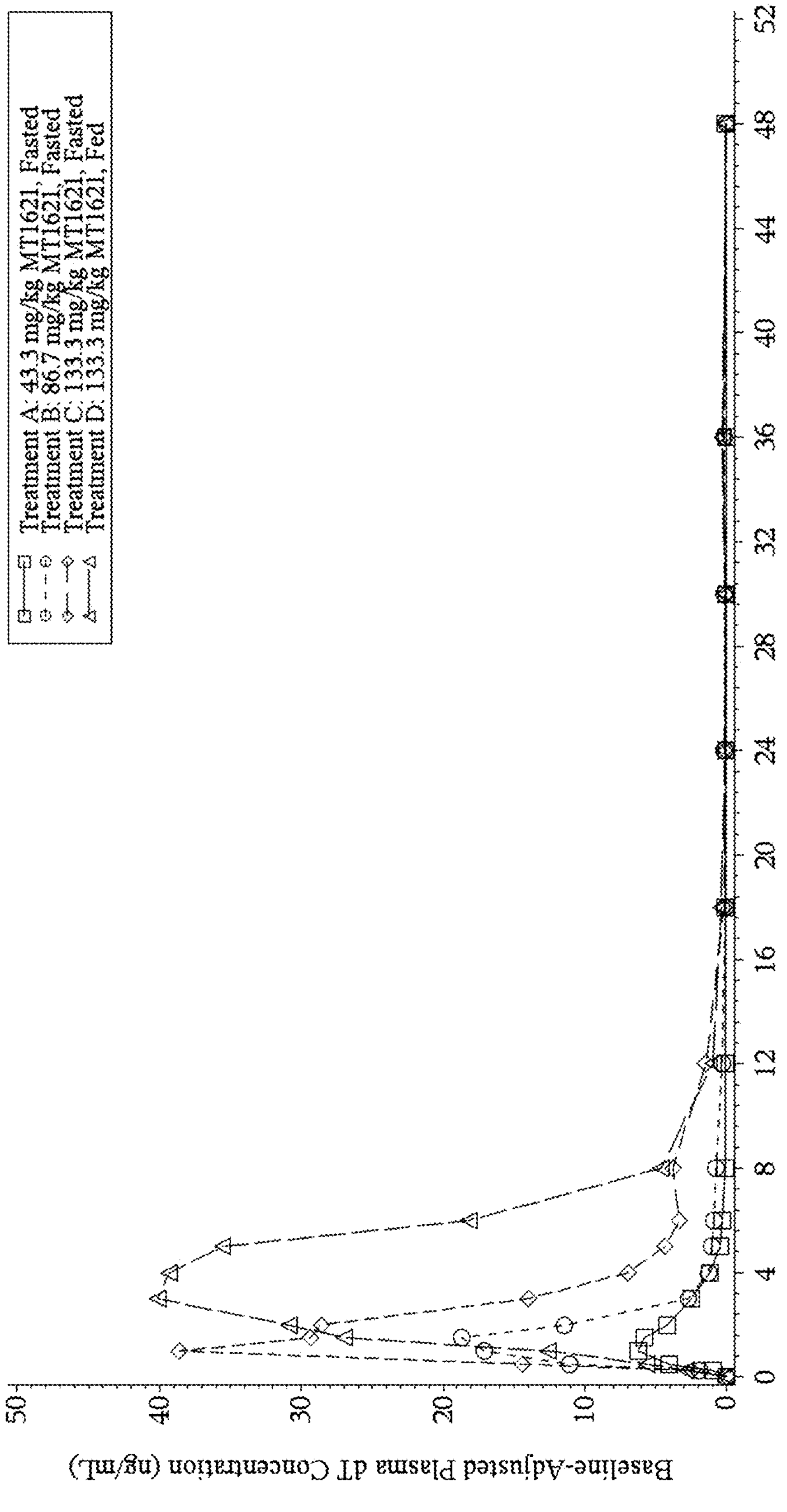
FIG. 4 shows a plot of baseline-adjusted arithmetic mean plasma dT concentration-time profiles following the administration of a single dose of 43.3 mg/kg MT1621 (i.e., 43.3 mg/kg of dC and 43.3 mg/kg of dT), Fasted, 86.7 mg/kg MT1621 (i.e., 86.7 mg/kg of dC and 86.7 mg/kg of dT), Fasted, 133.3 mg/kg MT1621 (i.e., 133.3 mg/kg dC and 133.3 mg/kg of dT), Fasted or 133.3 mg/kg MT1621 (i.e., 133.3 mg/kg dC and 133.3 mg/kg of dT), Fed in linear scale.
Figure 5:
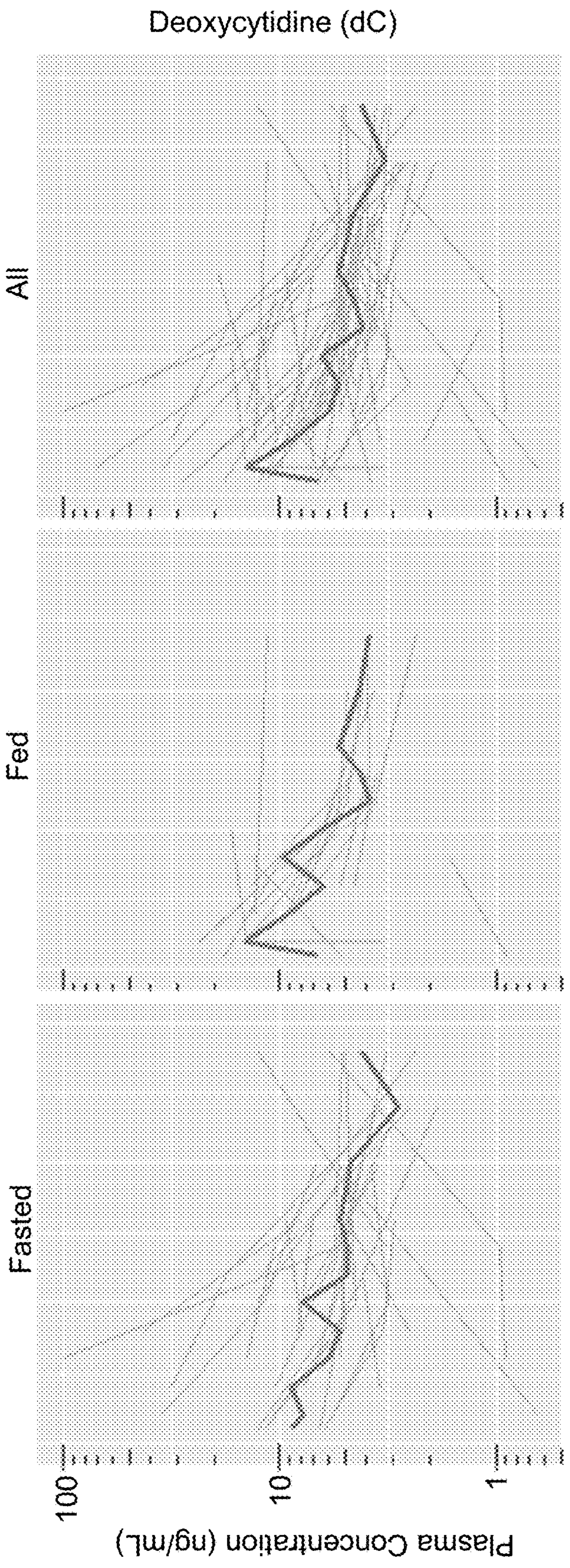
FIG. 5 shows a plot of nominal time after dose (hours) versus plasma concentration (ng/mL) for deoxycytidine (dC) measured in TK2 deficient subjects as described in Example 2.
Figure 6:
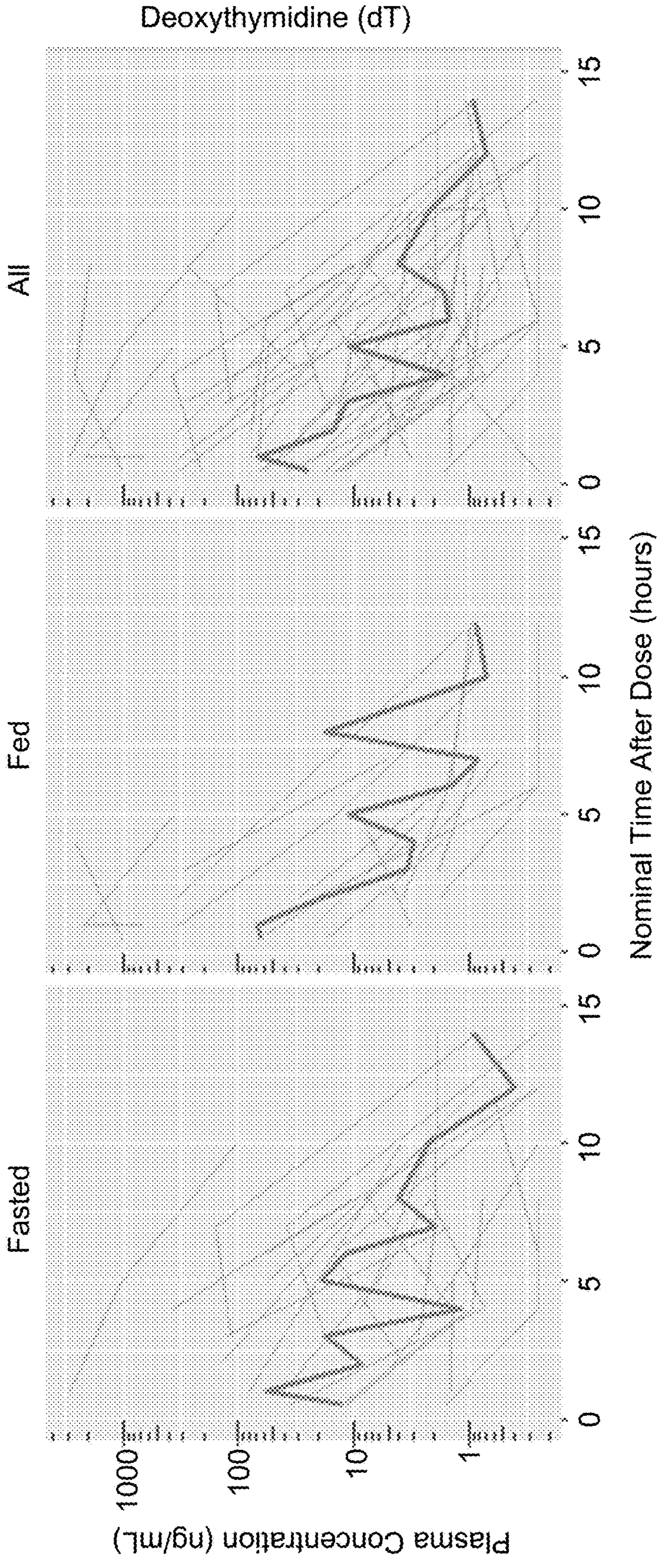
FIG. 6 shows a plot of nominal time after dose (hours) versus plasma concentration (ng/mL) for deoxythymidine (dT) measured in TK2 deficient subjects as described in Example 2.

Certain aspects of the current invention are based upon the surprising discovery that deoxythymidine and deoxycytidine have significantly altered pharmacokinetic measures of rate of absorption and plasma exposures when administered with food. The International Nonproprietary Name (INN) and the U.S. Adopted Name (USAN) for deoxythymidine is doxribtimine and the INN and USAN for deoxycytidine is doxecitine.

Definitions

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

Abbreviations of pharmacokinetic parameters calculated in the dosing studies and short definitions describing them as used herein are:

"Tmax" refers to the time to maximum concentration in a body fluid, such blood plasma.

"Cmax" refers to the observed maximum concentration in a body fluid, such blood plasma.

"Kel" refers to the slope of terminal linear portion of a plasma concentration/time curve.

"T½" refers to the half-life of a drug substance in a body fluid, such as blood plasma.

"AUC(0-t)" or "$AUC_{0-t}$" refers to an AUC measured from time 0 to the last measurable concentration.

AUC(last)" or $AUC_{last}$ refers to the area under the curve to last quantifiable concentration.

"AUC(0-inf)," "$AUC_{0-inf}$," or "AUC(0-infinity)" refers to the AUC value extrapolated to infinity.

The phrase "area under the curve" or "AUC" refers to a pharmacokinetic statistic used to describe the total exposure in a body fluid, such as blood plasma, or a tissue to a drug. More specifically, it is the time-averaged concentration of drug circulating in the body fluid analyzed (such as plasma, blood or serum). Standard calculation of AUC involves using non-compartmental techniques to calculate the AUC from time 0 to the last measurable concentration ($AUC_{0-t}$) and represents the observed overall exposure to a drug.

As used herein, the phrase "healthy subject" refers to a person who does not have a mitochondrial depletion syndrome.

The phrase "therapeutically effective amount" refers to the amount of a compound that, when administered to a subject for treating a disease, is sufficient to relieve to some extent one or more of the symptoms of the disease being treated, or result in inhibition of the progress or at least partial reversal of the disease. The "therapeutically effective amount" can vary depending on the compound, the disease and its severity, and the age, weight, etc., of the subject to be treated.

The term "bioavailability" refers to the extent of absorption of a drug that is absorbed systemically and is thus available to produce a biological effect.

The oral bioavailability fraction is $F_{oral}=F_{ABS}\times F_G\times F_H$, which is the fraction of the oral dose that reaches the circulation in an active, unchanged form. $F_{oral}$ is less than 100% of the active ingredient in the oral dose for three reasons: the drug is not absorbed through the GI tract and is eliminated in the feces; the drug is biotransformed by the cells of the intestine (to an inactive metabolite); or the drug is eliminated by the cells of the liver, either by biotransformation and/or by transport into the bile. Thus, "oral bioavailablity" is the product of the fraction of the oral dose that is absorbed ($F_{ABS}$), the fraction of the absorbed dose that successfully reaches the blood side of the gastrointestinal tract ($F_G$), and the fraction of the drug in the GI blood supply that reaches the heart side of the liver ($F_H$).

The phrase "food effect" refers to an unpredictable phenomenon in which food, or certain types of food, can influence the absorption of a drug from the gastrointestinal tract following oral administration. In some aspects, the food effect, as used herein, refers to a relative difference of at least 20% in AUC (area under the curve), Cmax (maximum plasma concentration), and/or Tmax (time at maximum concentration) of an active substance, when said substance or a formulation thereof, such as a tablet or capsule, is administered orally to a human subject, concomitantly with food, or in other words in a fed state as compared to when the same formulation is administered in a fasted state. The norms and guidelines of the U.S. Food and Drug Administration and the European Medicines Agency prescribe the administration of a large calorific intake of approximately 850-1000 kcal to check the fast-fed variability in the oral bioavailability of drugs under study. This meal should provide approximately 150 kcal of protein, 250 kcal of carbohydrate, and approximately 500-600 kcal of fat. See Rangaraj, N. et al., *Pharmaceutics* 14(9):1807 (2022).

A food effect can be designated negative when absorption is decreased, or positive when absorption is increased and manifested as an increase in oral bioavailability (as reflected by total exposure).

Alternatively, food effects can refer to changes in maximum concentration, or the time to reach maximum concentration, independently of overall absorption. As a result, some drugs are recommended to be taken in either fasted or fed conditions to achieve the optimum effect. For example, patients may be instructed to take a drug with a meal, before a meal (e.g., one hour before a meal), or after a meal (e.g., two hours after a meal). The pharmacokinetics of many drugs are unaffected by food, and they can be taken in either a fasted or a fed condition without an appreciable effect on pharmacokinetic parameters such as measures of rate and extent of absorption and exposure such as AUC, Cmax, Tmax, and T½.

As used herein, the term "fasted" refers to administration at least 4 hours after a meal. Moreover, a fasted state also requires continued fasting at least 2 hours after the administration.

As used herein, the term "high-fat" refers to the intake of food providing at least 500 kcals of fat.

The phrase "with food" refers to a condition of having consumed a solid food with sufficient bulk and fat content that it is not rapidly dissolved and absorbed in the stomach. In some embodiments, the food is a meal, such as breakfast, lunch, or dinner.

A food effect for the pyrimidine nucleosides was not expected based on a prior reported study of telbivudine. Telbivudine is 3-L-2-deoxythymidine, the non-natural enantiomer of deoxythymidine (β-D-2'-deoxythymidine); it was FDA-approved and EMA-approved for the treatment of hepatitis B viral infections. The study publication reported that values of Cmax, Tmax, and AUC were comparable when telbivudine (600-mg oral dose) was administered under fed and fasting conditions and that absorption of telbivudine as measured by Cmax, Tmax, AUC(0-t), and AUC(0-infinity) was not altered by food intake immediately before oral dosing. [Zhou X J, et al., J Clin Pharmacol. 2006 March; 46(3):275-81.]

In some embodiments, the Cmax of dC increases by between about 50% and about 100% when deoxycytidine and deoxythymidine are administered with food compared to when deoxycytidine and deoxythymidine are administered under fasted conditions. In some embodiments, the Cmax of dC increases by between about 50% and about 100%, between about 50% and about 90%, between about 50% and about 80%, between about 50% and about 70%, between about 50% and about 60%, between about 60% and about 100%, between about 60% and about 90%, between about 60% and about 80%, between about 60% and about 70%, between about 70% and about 100%, between about 70% and about 90%, between about 70% and about 80%, between about 80% and about 100%, between about 80% and about 90%, or between about 90% and 100% when deoxycytidine and deoxythymidine are administered with food compared to when deoxycytidine and deoxythymidine are administered under fasted conditions. In some embodiments, the Cmax of dC increases by at least about 50%, at least about 60%, at least about 70%, at least about 80%, at least about 90%, or at least about 100% when deoxycytidine and deoxythymidine are administered with food compared to when deoxycytidine and deoxythymidine are administered under fasted conditions. In some embodiments, the Cmax of dC increases by at least about 79% when deoxycytidine and deoxythymidine are administered with food compared to when deoxycytidine and deoxythymidine are administered under fasted conditions.

In some embodiments, the $AUC_{0-t}$ of dC increases by between about 110% and about 160% when deoxycytidine and deoxythymidine are administered with food compared to when deoxycytidine and deoxythymidine are administered under fasted conditions. In some embodiments, the $AUC_{0-t}$ of dC increases by between about 110% and about 160%, between about 110% and about 150%, between about 110% and about 140%, between about 110% and about 130%, between about 110% and about 120%, between about 120% and about 160%, between about 120% and about 150%, between about 120% and about 140%, between about 120% and about 130%, between about 130% and about 160%, between about 130% and about 150%, between about 130% and about 140%, between about 140% and about 160%, between about 140% and about 150%, or between about 150% and 160% when deoxycytidine and deoxythymidine are administered with food compared to when deoxycytidine and deoxythymidine are administered under fasted conditions. In some embodiments, the $AUC_{0-t}$ of dC increases by at least about 110%, at least about 120%, at least about 130%, at least about 140%, at least about 150%, or at least about 160% when deoxycytidine and deoxythymidine are administered with food compared to when deoxycytidine and deoxythymidine are administered under fasted conditions. In some embodiments, the $AUC_{0-t}$ of dC increases by at least about 137% when deoxycytidine and deoxythymidine are administered with food compared to when deoxycytidine and deoxythymidine are administered under fasted conditions.

In some embodiments, the Cmax of dT increases by between about 10% and about 60% when deoxycytidine and deoxythymidine are administered with food compared to when deoxycytidine and deoxythymidine are administered under fasted conditions. In some embodiments, the $AUC_{0-t}$ of dC increases by between about 10% and about 60%, between about 10% and about 50%, between about 10% and about 40%, between about 10% and about 30%, between about 10% and about 20%, between about 20% and about 60%, between about 20% and about 50%, between about 20% and about 40%, between about 20% and about 30%, between about 30% and about 60%, between about 30% and about 50%, between about 30% and about 40%, between about 40% to about 60%, between about 40% and about 50%, or between about 50% and 60% when deoxycytidine and deoxythymidine are administered with food compared to when deoxycytidine and deoxythymidine are administered under fasted conditions. In some embodiments, the Cmax of dT increases by at least about 10%, at least about 20%, at least about 30%, at least about 40%, at least about 50%, or at least about 60% when deoxycytidine and deoxythymidine are administered with food compared to when deoxycytidine and deoxythymidine are administered under fasted conditions. In some embodiments, the Cmax of dT increases by at least about 27% when deoxycytidine and deoxythymidine are administered with food compared to when deoxycytidine and deoxythymidine are administered under fasted conditions.

In some embodiments, the $AUC_{0-t}$ of dT increases by between about 50% and about 100% when deoxycytidine and deoxythymidine are administered with food compared to when deoxycytidine and deoxythymidine are administered under fasted conditions. In some embodiments, the $AUC_{0-t}$ of dT increases by between about 50% and about 100%, between about 50% and about 90%, between about 50% and about 80%, between about 50% and about 70%, between about 50% and about 60%, between about 60% and about 100%, between about 60% and about 90%, between about 60% and about 80%, between about 60% and about 70%, between about 70% and about 100%, between about 70% and about 90%, between about 70% and about 80%, between about 80% and about 100%, between about 80% and about 90%, or between about 90% and about 100% when deoxycytidine and deoxythymidine are administered with food compared to when deoxycytidine and deoxythymidine are administered under fasted conditions. In some embodiments, the $AUC_{0-t}$ of dT increases by at least about 50%, at least about 60%, at least about 70%, at least about 80%, at least about 90%, or at least about 100% when deoxycytidine and deoxythymidine are administered with food compared to when deoxycytidine and deoxythymidine are administered under fasted conditions. In some embodiments, the $AUC_{0-t}$ of dT increases by at least about 74% when deoxycytidine and deoxythymidine are administered with food compared to when deoxycytidine and deoxythymidine are administered under fasted conditions.

One aspect of this invention is a method of increasing the bioavailability of deoxycytidine in a human patient receiving deoxycytidine and deoxythymidine therapy when the nucleoside combination is administered with food. In an embodiment, the deoxycytidine and deoxythymidine therapy is administered at substantially the same time as the meal. In another embodiment, the deoxycytidine and deoxythymidine therapy is administered within 30 minutes before a meal. In some aspects, the administration to the patient occurs with the consumption of food or within 30 minutes or less (e.g., within 30, 29, 28, 27, 26, 25, 24, 23, 22, 21, 20, 19, 18, 17, 16, 15, 14, 13, 12, 11, 10, 8, 7, 6, 5, 4, 3, 2 or 1 minute(s)) prior to consumption of food. In another embodiment, the deoxycytidine and deoxythymidine therapy is administered within 2 hours after a meal. In some aspects, the administration to the patient occurs between about 1 hour prior to and about 2 hours after consuming food, between about 1 hour prior to and about 1.5 hours after consuming food, between about 1 hour prior to and about 1 hour after consuming food, between about 1 hour prior to and about 30 minutes after consuming food, between about 30 minutes prior to and about 2 hours after consuming food, between about 30 minutes prior to and about 1.5 hours after consuming food, between about 30 minutes prior to and about 1 hour after consuming food, or between about 30 minutes prior to and about 30 minutes after consuming food. In some aspects, the administration to the patient is with or immediately after the consumption of food up to 1 hour after said consumption (e.g., 0 minutes to 1 hour).

Another aspect of this invention is a method of increasing the rate of absorption of deoxycytidine in a human patient receiving deoxycytidine and deoxythymidine therapy when the nucleoside combination is administered with food. In an embodiment, the deoxycytidine and deoxythymidine therapy is administered at substantially the same time as the meal. In another embodiment, the deoxycytidine and deoxythymidine therapy is administered within 30 minutes before a meal. In another embodiment, the deoxycytidine and deoxythymidine therapy is administered within 2 hours after a meal. In an embodiment, the meal is a high-fat, high calorie meal. In another embodiment the meal is adapted to individual patient's digestive health with the aim of providing as much fat and caloric content as possible.

Another aspect of this invention is a method of increasing the bioavailability of deoxythymidine in a human patient receiving deoxycytidine and deoxythymidine therapy when the nucleoside combination is administered with food. In an embodiment, the deoxycytidine and deoxythymidine therapy is administered at substantially the same time as the meal. In another embodiment, the deoxycytidine and deoxythymidine therapy is administered within 30 minutes before a meal. In another embodiment, the deoxycytidine and deoxythymidine therapy is administered within 2 hours after a meal.

Another aspect of the invention is providing a method of increasing rate and extent of absorption as measured by the drug concentration attained in the blood stream over time of a patient receiving the drug via oral dosage which method comprises administering a therapeutically effective amount of deoxycytidine to the patient with food.

Another aspect of the invention is providing a method of treating a patient with deoxycytidine and deoxythymidine therapy and reducing or eliminating gastrointestinal side effects by administering the therapy with food. In an embodiment, the deoxycytidine and deoxythymidine therapy is administered at substantially the same time as the meal. In another embodiment, the deoxycytidine and deoxythymidine therapy is administered within 30 minutes before a meal. In another embodiment, the deoxycytidine and deoxythymidine therapy is administered within 2 hours after a meal. In another embodiment the gastrointestinal side effects are one or more of nausea, vomiting, and diarrhea.

In another aspect, dose ranges for administration with food are from about 50 mg/kg/day (i.e, about 50 mg/kg/day of dC and about 50 mg/kg/day of dT) to about 500 mg/kg/day (i.e., about 500 mg/kg/day of dC and 500 mg/kg/day of dT). Doses can be adjusted to optimize the effects in the subject. For example, the deoxynucleosides can be administered at 100 mg/kg/day to start, and then 30 mg/kg/day increased over time to 200 mg/kg/day, to 400 mg/kg/day, to 800 mg/kg/day, up to 1000 mg/kg/day, depending upon the subject's response and tolerability. In an embodiment the deoxynucleosides can be administered from about 200 mg/kg/day to 600 mg/kg/day. In an embodiment of the invention, a daily dose is up to a target or maintenance dose of 400 mg/kg/day of a substantially equal mixture of dC and dT (weight for weight), and is administered with food, and optionally reduced based on tolerability of the dose by the patient. In a further embodiment, the dose is divided by approximately one-third of the preferred daily dose and administered three times daily (TID) with food. A subject can also be monitored for any adverse effects, such as gastrointestinal intolerance, e.g., diarrhea, and monitored for improvement when the treatment is administered with food. In some embodiments, one or more doses per day are administered with food. In some embodiments, two or more doses per day are administered with food. In some embodiments, three doses per day are administered with food. In some embodiments, when three doses are administered per day, at least one dose is administered with food. In some embodiments, when three doses are administered per day, at least two doses are administered with food. In some embodiments, when three doses are administered per day, three doses are administered with food. In some embodiments, one dose per day is administered with food. In some embodiments, two doses per day are administered with food. In some embodiments, three doses per day are administered with food.

In some embodiments, a total daily dose of dC and dT contains equals parts by weight of dC and dT. In some embodiments, the total daily dose of the combined weight of dC and dT containing equal parts by weight of dC and dT is between about 50 mg/kg and about 1000 mg/kg, between about 50 mg/kg and about 800 mg/kg, between about 50 mg/kg and about 600 mg/kg, between about 50 mg/kg and about 500 mg/kg, between about 50 mg/kg and about 400 mg/kg, between about 50 mg/kg and about 200 mg/kg, between about 50 mg/kg and about 100 mg/kg, between about 100 mg/kg and about 1000 mg/kg, between about 100 mg/kg and about 800 mg/kg, between about 100 mg/kg and about 600 mg/kg, between about 100 mg/kg and about 500 mg/kg, between about 100 mg/kg and about 400 mg/kg, between about 100 mg/kg and about 200 mg/kg, between about 200 mg/kg and about 1000 mg/kg, between about 200 mg/kg and about 800 mg/kg, between about 200 mg/kg and about 600 mg/kg, between about 200 mg/kg and about 500 mg/kg, between about 200 mg/kg and about 400 mg/kg, between about 400 mg/kg and about 1000 mg/kg, between about 400 mg/kg and about 800 mg/kg, between about 400 mg/kg and about 600 mg/kg, between about 400 mg/kg and about 500 mg/kg, between about 500 mg/kg and about 1000 mg/kg, between about 500 mg/kg and about 800 mg/kg, between about 500 mg/kg and about 600 mg/kg, between about 600 mg/kg and about 1000 mg/kg, between about 600 mg/kg and about 800 mg/kg, or between about 800 mg/kg and about 1000 mg/kg.

In some embodiments, the total daily dose is divided equally into three separate doses of dC and dT, wherein each dose of dC and dT is separately administered over a 24-hour period. In some embodiments, each separate dose contains equal parts by weight of dC and dT and the dC and dT are administered separately but substantially simultaneously. In some embodiments, each dose contains equal parts by weight of dC and dT and the dC and dT are combined before administration. In some embodiments, each dose contains equal parts by weight of dC and dT and the dC and dT are combined as a fixed dose combination pharmaceutical composition in a single packet.

In some embodiments, the total daily dose comprises three separate doses of dC and dT, each dose administered at a different time in a 24-hour period, wherein each dose contains equal parts by weight of dC and dT. In some embodiments, each dose contains as a combined weight of dC and dT, wherein dC and dT are in equal parts by weight, between about 15 mg/kg and about 330 mg/kg, between about 15 mg/kg and about 260 mg/kg, between about 15 mg/kg and about 200 mg/kg, between about 15 mg/kg and about 160 mg/kg, between about 15 mg/kg and about 133 mg/kg, between about 15 mg/kg and about 70 mg/kg, between about 15 mg/kg and about 33 mg/kg, between about 33 mg/kg and about 330 mg/kg, between about 33 mg/kg and about 260 mg/kg, between about 33 mg/kg and about 200 mg/kg, between about 33 mg/kg and about 160 mg/kg, between about 33 mg/kg and about 133 mg/kg, between about 33 mg/kg and about 70 mg/kg, between about 70 mg/kg and about 330 mg/kg, between about 70 mg/kg and about 260 mg/kg, between about 70 mg/kg and about 200 mg/kg, between about 70 mg/kg and about 160 mg/kg, between about 70 mg/kg and about 133 mg/kg, between about 133 mg/kg and about 330 mg/kg, between about 133 mg/kg and about 260 mg/kg, between about 133 mg/kg and about 200 mg/kg, between about 133 mg/kg and about 160 mg/kg, between about 160 mg/kg and about 330 mg/kg, between about 160 mg/kg and about 260 mg/kg, between about 160 mg/kg and about 200 mg/kg, between about 200 mg/kg and about 330 mg/kg, between about 200 mg/kg and about 260 mg/kg, or between about 260 mg/kg and about 330 mg/kg, wherein three doses are administered over a 24-hour period. In some embodiments, each dose contains as a combined weight of dC and dT, wherein dC and dT are in equal parts by weight, about 330 mg/kg, about 260 mg/kg, about 200 mg/kg, about 160 mg/kg, about 133 mg/kg, about 70 mg/kg, about 33 mg/kg, or about 15 mg/kg, wherein three doses are administered over a 24-hour period.

In an aspect, the efficacy of the treatment to a patient for a MDS is increased by administering the target daily doses of dC and dT with food.

In another aspect, dose ranges of each of the nucleosides can be reduced to take account of the increased bioavailability of the deoxynucleosides when administered with food. In an embodiment, lowering the daily dose of the deoxynucleosides reduces gastrointestinal intolerance. In another aspect, dosing volumes of each of the nucleosides can be reduced to account for the increased bioavailability of the deoxynucleosides when administered with food.

Routes of Administration

In an embodiment, the deoxycytidine and deoxythymidine therapy is administered orally. In another embodiment, the deoxycytidine and deoxythymidine therapy is dissolved in water or juice to provide a solution for oral administration. In an embodiment, the solution is administered via a dispensing device which may be a syringe or graduated pipette useful for measuring varying doses and delivering the dose of the solution of drug product. In an embodiment, a dispensing device is used as a metered dosing device capable of dispensing a fixed volume of the solution of drug product. In an embodiment, the deoxycytidine and deoxythymidine therapy is administered by feeding tube. In some embodiments, the feeding tube is a nasogastric feeding tube or an enteric feeding tube.

Dosage Form/Frequency of Administration

In an MT1621 clinical development program, two formulations were considered. The first formulation consisted of dC and dT supplied in separate packets, to be combined before dosing. The second formulation, the formulation in which MT1621 therapy is supplied for clinical studies, consisted of a fixed dose combination of dC and dT supplied in a single packet. Pharmacokinetic (PK) considerations in the clinical development program include the dosing frequency of 3 divided doses/day, rate, and extent of dC and dT absorption, the effect of food on PK and tolerability, dose proportionality of both formulations, and renal clearance.

Example 1. Open-Label, Fixed-Sequence, Single-Ascending Dose Study in Adult Healthy Subjects Designed to Evaluate the Safety, Tolerability, PK, and Food-Effect of MT1621

A phase 1 study was conducted as an open-label, fixed-sequence, single-ascending dose study in adult healthy subjects designed to evaluate the safety, tolerability, PK, and food-effect of MT1621 (dC and dT). To evaluate the PK of MT1621, the combination was administered at three different doses. Treatment A was a 43.3 mg/kg dose of MT1621 (i.e., a 43.3 mg/kg dose of dC and a 43.3 mg/kg dose of dT (each approximately equivalent to 1 dose of a 130 mg/kg daily dose, divided 3 times daily [TID])) in healthy male and female subjects under fasting conditions; Treatment B was an 86.7 mg/kg dose of MT1621 (i.e., a 86.7 mg/kg dose of dC and a 86.7 mg/kg dose of dT (each approximately equivalent to 1 dose of a 260 mg/kg daily dose, divided TID)) in healthy male and female subjects under fasting conditions; and Treatment C was a 133.3 mg/kg dose of MT1621 (i.e., a 133.3 mg/kg dose of dC and a 133.3 mg/kg dose of dT (each approximately equivalent to a 400 mg/kg daily dose, divided TID)) in healthy male and female subjects under fasting conditions. Additionally, Treatment D was a 133.3 mg/kg dose of MT1621 (i.e., a 133.3 mg/kg dose of dC and a 133.3 mg/kg dose of dT (each approximately equivalent to a 400 mg/kg daily dose, divided TID) in healthy male and female subjects under fed conditions, to determine the effect of a high-fat meal on the single-dose PK of MT1621.

Methodology of open-label, Phase 1, fixed-sequence, single-dose, dose escalation, and food-effect study. Fourteen (14) healthy, adult, male and female subjects were enrolled with an approximately equal distribution (at least 40% of each sex) between male and female subjects.

Screening of subjects occurred within 28 days prior to the first dosing.

On Day 1 of each period, subjects received 1 of 3 dose levels of MT1621 under fasting conditions as escalating single doses over 3 periods in Part A (Treatments A, B, and C in Periods 1, 2, and 3, respectively) and with the highest dose under fed conditions in Part B (Treatment D in Period 4). Four (4) of 14 subjects that completed Part A (Periods 1 to 3) could not complete Part B (Treatment D in Period 4) during the original confinement. These subjects were then to return to the clinical unit and continue the study to complete Part B (Treatment D in Period 4); 2 of the 4 subjects completed Part B.

Each treatment was assessed by blood and urine PK sampling pre-dose and up to 48 hours post-dose for the determination of dC and dT in plasma and urine PK, and possible future analysis of blood for PD biomarkers.

Dose escalation to the next dose level (i.e., next period) did not take place until it was determined that adequate safety and tolerability had been demonstrated regarding the previous dose level(s) to permit proceeding to the next dose level.

A washout period of at least 2 days without drug between each treatment administration was maintained. Fourteen subjects were enrolled in the study, and 12 subjects completed the study. Data from 14 subjects were included in the PK analysis of Periods 1, 2, and 3 and data from 12 subjects were included in the PK analysis of Period 4.

Study drug administered in Example 1 was 0.5 g dC and 0.5 g dT powders for solution and were reconstituted in juice or water.

After reconstitution in a fixed amount of water or juice, the solution was administered via measured volume to provide the amounts specified in Studies A, B, C, and D.

Active ingredients and excipients in the drug product under development are as shown in Table 1.

Packets providing the target daily dose and dissolved in water or juice once per day and volumes corresponding to the mg/kg needed for the divided doses are withdrawn for multi-dose administration.

TABLE 1

| Ingredient | | (mg per mixed sachet) | Composition |
|---|---|---|---|
| 2'-Deoxycytidine | Drug substance | 2000.00 | 48.25 |
| 2'-Deoxythymidine | Drug substance | 2000.00 | 48.25 |
| Silica Colloidal Anhydrous (Aerosil 200) | Glidant | 124.352 | 3.00 |
| Magnesium Stearate | Lubricant | 20.725 | 0.50 |
| Total: | | 4145.08 | 100.0 |

MT1621 was administered orally at Hour 0 on Day 1, following an overnight fast for Treatments A, B, and C and within 5 minutes of consumption of a standardized high-fat breakfast (which included eggs, bacon, and toast with butter) for Treatment D.

Pharmacokinetics:

Blood samples for the determination of plasma dC and dT concentrations were collected on Day 1 of each period at pre-dose (0 hour), and at 0.25, 0.5, 1, 1.5, 2, 3, 4, 5, 6, 8, 12, 24, and 48 after study drug administration. In Period 4, blood was collected for the 48-hour PK sample; for Periods 1 through 3, the 48-hour PK sample was collected at the same time as the pre-dose PK sample from the next period so only 1 sample was collected for both PK time points. It should be pointed out that Periods 1-3 used sampling up to 24 hours for PK while Period 4 used the complete 48-hour profile.

Urine samples for the determination of dC and dT concentrations were collected at Predose (up to 2 hours before dosing) and 0-4 hours, 4-8 hours, 8-12 hours, 12-24 hours, and 24-48 hours after dosing.

The following noncompartmental PK parameters for plasma dC and dT were determined: area under the curve from time zero to last observed/measured non-zero concentration ($AUC_{0-t}$), area under the concentration-time curve from time zero extrapolated to infinity (AUC0-inf), area under the concentration-time curve during dosing interval (AUCtau), the maximum observed concentration (Cmax), the time to reach Cmax (Tmax), apparent terminal elimination rate constant (Kel) representing the fraction of drug eliminated per unit time, apparent terminal elimination half-life of drug in plasma (t½, the apparent total plasma clearance after extravascular administration (CL/F), and the apparent volume of distribution during the terminal elimination phase after extravascular administration (Vz/F).

The following urinary PK parameters were presented for dC and dT: drug concentration in the urine during the urine collection interval (Cur), volume of urine collected over the entire urine collection interval (Vur), amount of unchanged drug excreted in the urine (Ae), cumulative amount of unchanged drug excreted in the urine (Ae,Cum), fraction (in percentage) of dose excreted into urine (fe), and renal clearance calculated as the ratio of cumulative amount excreted in urine to plasma area under the curve (CLr).

For the calculation of the PK parameters, raw (unadjusted) plasma dC and dT concentrations below the limit of quantitation (BLQ) were set to ½ the limit of quantitation (LOQ) of the assay throughout the PK profile if the majority of subjects displayed measurable pre-dose (endogenous baseline) concentrations. Since all subjects had measurable pre-dose (endogenous baseline) concentrations, Kel and associated PK parameters were not calculated for unadjusted data.

Method of Baseline-Adjustment of Plasma Pharmacokinetic Parameters

Predose blood samples for each dose level (each treatment period) served as confirmation of sufficient washout between dose levels and were also used to determine the amount of endogenous dC and dT. Each subject had 3 pre-dose samples (−2, −1, and −0.25 [−0.583] hours). Baseline adjustments were performed in all subjects regardless of the magnitude of their pre-dose values. Given the anticipated short T½ for dC and dT, no carryover effect from the exogenous MT1621 administration was expected in this single-dose study.

Baseline adjustments were conducted by subtracting the arithmetic mean baseline (mean of all 3 pre-dose concentrations) in each subject by treatment period from every postdose plasma dC and dT concentration prior to calculating the adjusted PK parameters. This was on a per-subject and per-period basis. All negative values after baseline adjustment were set to zero.

Bioanalytical Procedures

Plasma: dC and dT were quantified using a validated high-performance liquid chromatography with tandem mass spectrometry (LC-MS/MS) method. dC and dT were extracted from plasma samples by a single solid phase extraction procedure. The extracts were injected once using Syneos Health high performance liquid chromatography (HPLC) method TM.2541 for dC and injected again using Syneos Health HPLC method TM.2547 for dT. The 2 methods for the determination of dC and dT in human plasma were validated in accordance with the 2018 FDA guidance and the 2011 EMA guidance on bioanalytical method validation. The methods demonstrate acceptable sensitivity, selectivity, precision, and accuracy for the quantification of dC and dT over a range from 0.500 to 200 ng/mL for each analyte (low limit of quantification [LLOQ] of 0.5 ng/mL in 0.200 mL tetrahydrouridine and sodium citrate) stabilized dipotassium ethylenediaminetetraacetic acid (K2EDTA)-treated human plasma by liquid chromatography electrospray ionization tandem mass spectrometric (LC/ESI/MS/MS) in positive ion mode using [15N3]-deoxycytidine and [D3]-deoxythymidine as the internal standards (IS), respectively.

Statistical Methods:

The plasma and urine concentrations of dC and dT were listed and summarized by treatment and time point for all subjects in the PK population group. Summary statistics, including sample size (N), arithmetic mean (Mean), standard deviation (SD), coefficient of variation (CV %), minimum (Min), median, maximum (Max), geometric mean (GM), and geometric CV % (GMCV[%]) were calculated for all nominal concentration time points and PK parameters.

The food-effect assessment was conducted only on data from subjects who completed the study or had sufficient data for a pairwise comparison.

An analysis of variance (ANOVA) was performed on natural log (ln)-transformed plasma PK parameters $AUC_{0-t}$ and Cmax for original and baseline-adjusted plasma dC and dT concentrations.

The ANOVA model included dietary conditions (fasting, fed) as a fixed effect and subject as a random effect. Each ANOVA included calculation of least-squares means (LSMs), the difference between regimen LSMs, and the standard error associated with this difference.

Ratios of LSM were calculated using the exponentiation of the LSM from the analyses on the natural log transformed to fasting conditions.

Dose proportionality was evaluated for original and baseline-adjusted plasma dC and dT, AUC0-inf, $AUC_{0-t}$, and Cmax parameters following administration of single doses (fasted Treatments A, B, and C).

$AUC_{0-t}$ and Cmax. These ratios were expressed as a percentage relative to fasting conditions (i.e., Treatment D/Treatment C).

Consistent with the two one-sided test, 90% confidence intervals (CIs) for the ratios were derived by exponentiation of the CIs obtained for the difference between regimen LSM resulting from the analyses on the ln-transformed $AUC_{0-t}$ and Cmax. The CIs were expressed as a percentage relative to fasting conditions.

Dose proportionality was evaluated for original and baseline-adjusted plasma dC and dT AUC0-inf, $AUC_{0-t}$, and Cmax parameters following administration of single doses (fasted treatments A, B, and C).

Food-Effect Assessment

The food-effect assessment was conducted only on data from subjects who completed the study or had sufficient data for a pairwise comparison.

An analysis of variance (ANOVA) was performed on the baseline corrected natural log (ln)-transformed plasma PK parameters AUC0-t and Cmax. The ANOVA model included dietary regimens (fasting, fed) as a fixed effect and subject as a random effect. Each ANOVA included calculation of least-squares means ("LSM"), the difference between regimen LSM, and the standard error associated with this difference.

Ratios of LSM were calculated using the exponentiation of the LSM from the analyses on the ln-transformed AUC0-t and Cmax. These ratios were expressed as a percentage relative to fasting conditions (i.e., Treatment D/Treatment C).

Consistent with the two one-sided test, 90% confidence intervals (CIs) for the ratios were derived by exponentiation of the CIs obtained for the difference between regimen LSM resulting from the analyses on the ln-transformed AUC0-t and Cmax. The CIs were expressed as a percentage relative to fasting conditions (i.e., Treatment D/Treatment C).

If baseline adjustments were appropriate (i.e., pre-dose dC and dT concentrations were measurable in the majority of subjects), then this analysis was also performed on baseline adjusted PK parameters AUC0-t, AUC0-inf, and Cmax.

Dose Proportionality Analysis

Dose-proportionality was evaluated for original and baseline-corrected plasma dC and dT AUC0-t and Cmax parameters following administration of single doses (fasted Treatments A, B, and C). To evaluate dose proportionality, a linear regression and power model approach were used.

First, a linear relationship between the PK parameters AUC0-t and Cmax and the dose were fitted using a regression that includes both linear (β1) and quadratic (β2) effect terms:

$$Y=\alpha+\beta 1^{*}Dose+\beta 2^{*}Dose2+\varepsilon,$$

where Y represented the natural log of the PK parameters, AUC0-t, AUC0-inf, and Cmax. and ε accounts for measurement errors in the independent variables. If β2 or α deviated from zero, dose proportionality was not declared. If β2 was not significantly different from zero, the linear regression was simplified as:

$$Y=\alpha+\beta^{*}Dose+\varepsilon$$

The slope, β, measured the dose proportionality between dose and the dose-dependent PK parameter. Dose proportionality required β=1.

Thus, as the second step, the 95. CIs for the slope β corresponding to the in-transformed PK parameters, were calculated. Dose proportionality was established if the 9500 CIs included the value of 1 for dose-dependent parameters (AUC0-t and Cmax).

Since baseline adjustments were performed (i.e., pre-dose dC and dT concentrations were measurable in the majority of subjects), then this analysis was also performed on baseline-adjusted PK parameters AUC0-t and Cmax.

TABLE 2

Summary of Baseline-Adjusted Plasma dC Pharmacokinetic Parameters Following the Administration of a Single Dose of 43.3 mg/kg MT1621, Fasted (A); 86.7 mg/kg MT1621, Fasted, (B); 133.3 mg/kg MT1621, Fasted (C); and 133.3 mg/kg MT1621, Fed (D) - Part 2 (PK Evaluable Population)

| Pharmacokinetic Parameters | A | B | C | D |
|---|---|---|---|---|
| AUC0-4 | 7.840 (78.5) | 10.31 (60.6) | 17.15 (73.3) | 31.66 (68.8) |
| (ng*hr/mL) | [n = 14] | [n = 14] | [n = 14] | [n = 14] |
| AUC0-6 | 9.580 (86.8) | 12.79 (60.0) | 21.10 (78.0) | 48.16 (73.0) |
| (ng*hr/mL) | [n = 14] | [n = 14] | [n = 14] | [n = 14] |
| AUC0-t | 13.49 (94.1) | 23.23 (66.7) | 30.79 (76.5) | 73.03 (71.7) |
| (ng*hr/mL) | [n = 14] | [n = 14] | [n = 14] | [n = 14] |
| AUC0-48 | 19.57 (82.2) | 29.43 (51.7) | 53.14 (61.1) | 55.80 (57.6) |
| (ng*hr/mL) | [n = 6] | [n = 9] | [n = 5] | [n = 9] |
| AUC0-inf | 48.38 (73.8) | 26.62 (94.0) | 22.52 (34.6) | 137.9 (57.7) |
| (ng*hr/mL) | [n = 3] | [n = 5] | [n = 4] | [n = 2] |
| AUC%extrap (%) | 11.36 ± 8.5281 | 12.46 ± 13.194 | 1.152 ± 1.0948 | 3.567 ± 5.0087 |
| | [n = 3] | [n = 5] | [n = 4] | [n = 2] |

TABLE 2-continued

Summary of Baseline-Adjusted Plasma dC Pharmacokinetic Parameters Following the Administration of a Single Dose of 43.3 mg/kg MT1621, Fasted (A); 86.7 mg/kg MT1621, Fasted, (B); 133.3 mg/kg MT1621, Fasted (C); and 133.3 mg/kg MT1621, Fed (D) - Part 2 (PK Evaluable Population)

| Pharmacokinetic Parameters | A | B | C | D |
|---|---|---|---|---|
| Cmax (ng/ml) | 3.527 (83.1) [n = 14] | 4.675 (65.9) [n = 14] | 7.168 (73.0) [n = 14] | 12.82 (77.9) [n = 14] |
| Tmax (hr) | 1.249 (0.25,3.00) [n = 14] | 1.510 (0.26, 4.00) [n = 14] | 1.257 (0.50, 3.00) [n = 14] | 2.016 (0.51, 6.00) [n = 14] |
| Kel (1/hr) | 0.1280 ± 0.12759 [n = 3] | 0.2030 ± 0.19382 [n = 5] | 0.4884 ± 0 .45579 [n = 4] | 0.7971 ± 0.38688 [n = 2] |
| t½ (hr) | 10.278 ± 8.1960 [n = 3] | 8.624 ± 8.6836 [n = 5] | 2.671 ± 1.9783 [n = 4] | 0.986 ± 0.4784 [n = 2] |
| CL/F (L/hr/kg) | 1033 ± 669.41 [n = 3] | 4184 ± 3366.0 [n = 5] | 6167 ± 1978.3 [n = 4] | 1037 ± 530.76 [n = 2] |
| Vz/F (L/kg) | 10330 ± 3402.8 [n = 3] | 38260 ± 32282 [n = 5] | 19790 ± 11151 [n = 4] | 1657 ± 1470.4 [n = 2] |

Treatment A: (43.3 mg/kg dose), at Hour 0 on Day 1, following an overnight fast
Treatment B: (86.7 mg/kg dose), at Hour 0 on Day 1, following an overnight fast
Treatment C: (133.3 mg/kg dose), at Hour 0 on Day 1, following an overnight fast
Treatment D: (133.3 mg/kg) dose, within 5 minutes of consumption of the standard high-fat breakfast meal, at Hour 0 on Day 1
AUCs and Cmax are presented as geometric mean (geometric coefficient of variation % (CV %))
Tmax is presented as median (minimum, maximum)
Other parameters are presented as arithmetic mean ± SD

TABLE 3

Summary of Baseline-Adjusted Plasma dT Pharmacokinetic Parameters Following the Administration of a Single Dose of 43.3 mg/kg MT1621, Fasted (A); 86.7 mg/kg MT1621, Fasted, (B); 133.3 mg/kg MT1621, Fasted (C); and 133.3 mg/kg MT1621, Fed (D) Part 2 (PK Evaluable Population)

| Pharmacokinetic Parameters | A | B | C | D |
|---|---|---|---|---|
| AUC0-4 (ng*hr/mL) | 8.780 (142.5) [n = 13] | 21.03 (172.1) [n = 14] | 53.13 (168.0) [n = 14] | 74.39 (124.0) [n = 14] |
| AUC0-6 (ng*hr/mL) | 11.12 (122.2) [n = 12] | 23.15 (159.9) [n = 14] | 60.59 (166.3) [n = 14] | 118.7 (126.8) [n = 14] |
| AUC0-t (ng*hr/mL) | 12.56 (124.9) [n = 13] | 31.71 (126.6) [n = 14] | 91.15 (94.1) [n = 14] | 158.9 (101.4) [n = 14] |
| AUC0-48 (ng*hr/mL) | 18.19 (102.9) [n = 7] | 82.09 (46.5) [n = 2] | 113.5 (31.4) [n = 2] | 140.8 (72.6) [n = 5] |
| AUC0-inf (ng*hr/mL) | 3.556 (NC) [n = 1] | 67.15 (51.2) [n = 3] | 144.1 (6.9) [n = 3] | 149.4 (135.7) [n = 5] |
| AUC%extrap (%) | 46.24 ± NC [n = 1] | 6.481 ± 5.9830 [n = 3] | 1.954 ± 1.6169 [n = 3] | 1.244 ± 1.1349 [n = 5] |
| Cmax (ng/ml) | 6.190 (107.8) [n = 13] | 14.18 (156.9) [n = 14] | 31.50 (119.6) [n = 14] | 40.13 (102.9) [n = 14] |
| Tmax (hr) | 0.516 (0.50, 2.00) [n = 13] | 1.059 (0.26, 2.05) [n = 14] | 1.255 (1.00, 12.02) [n-14] | 4.001 (1.50, 8.00) [n = 14] |
| Kel (1/hr) | 0.1569 ± NC [n = 1] | 0.09320 ± 0.072046 [n = 3] | 0.09785 ± 0.060940 [n = 3] | 0.2445 ± 0.28626 [n = 5] |
| t½ (hr) | 4.417 ± NC [n = 1] | 10.420 ± 5.9502 [n = 3] | 8.755 ± 4.0359 [n = 3] | 5.349 ± 3.1148 [n = 5] |
| CL/F (L/hr/kg) | 12180 ± NC [n = 1] | 1384 ± 562.78 [n = 3] | 926.5 ± 63.855 [n = 3] | 1390 ± 1575.7 [n = 5] |
| Vz/F (L/kg) | 77600 ± NC [n = 1] | 23970 ± 18329 [n = 3] | 11920 ± 5975.6 [n = 3] | 6222 ± 2876.0 [n = 5] |

Treatment A: (43.3 mg/kg dose), at Hour 0 on Day 1, following an overnight fast
Treatment B: (86.7 mg/kg dose), at Hour 0 on Day 1, following an overnight fast
Treatment C: (133.3 mg/kg dose), at Hour 0 on Day 1, following an overnight fast
Treatment D: 133.3 mg/kg dose), within 5 minutes of consumption of the standard high-fat breakfast meal, at Hour 0 on Day 1
NC = Not calculated
AUCs and Cmax are presented as geometric mean (geometric coefficient of variation % (CV %)
Tmax is presented as median (minimum, maximum)
Other parameters are presented as arithmetic mean ± SD

TABLE 4

Statistical Comparisons of Baseline-Adjusted Plasma dC Pharmacokinetic Parameters: 133.3 mg/kg MT1621, Fed Versus 133.3 mg/kg MT1621, Fasted - Part 2 (PK Population)

| | 133.3 mg/kg MT1621, Fed (Test) | | 133.3 mg/kg MT1621, Fasted (Reference) | | | 90% | Intra- |
|---|---|---|---|---|---|---|---|
| Parameter | Geometric LSM | n | Geometric LSM | n | GMR (%) | Confidence Interval | subject CV % |
| AUC0-t (ng*hr/mL) | 73.03 | 14 | 30.79 | 14 | 237.18 | 182.93-307.51 | 42.5 |
| Cmax (ng/ml) | 12.82 | 14 | 7.168 | 14 | 178.88 | 142.21-224.99 | 37.2 |

Treatment D: 133.3 mg/kg dose of MT1621, within 5 minutes of consumption of the standard high-fat breakfast meal, at Hour 0 on Day 1 (test)

Treatment C: 133.3 mg/kg dose of MT1621, at Hour 0 on Day 1, following an overnight fast (reference)

Parameters were ln-transformed prior to analysis.

Geometric least-squares means (LSMs) are calculated by exponentiating the LSMs from the ANOVA.

Geometric Mean Ratio (GMR) = 100*(test/reference)

Intra-subject CV % was calculated as 100*square root(exp[MSE] − 1), where MSE = residual variance from ANOVA.

TABLE 5

Statistical Comparisons of Baseline-Adjusted Plasma dT Pharmacokinetic Parameters: 133.3 mg/kg MT1621, Fed Versus 133.3 mg/kg MT1621, Fasted - Part 2 (PK Population)

| | 133.3 mg/kg MT1621, Fed (Test) | | 133.3 mg/kg MT1621, Fasted (Reference) | | | 90% | |
|---|---|---|---|---|---|---|---|
| Parameter | Geometric LSM | n | Geometric LSM | n | GMR (%) | Confidence Interval | Intra-subject CV % |
| AUC0-t (ng*hr/mL) | 158.9 | 14 | 91.15 | 14 | 174.38 | 135.73-224.03 | 40.9 |
| Cmax (ng/ml) | 40.13 | 14 | 31.50 | 14 | 127.39 | 99.16-163.65 | 40.9 |

Treatment D: 133.3 mg/kg dose of MT1621, within 5 minutes of consumption of the standard high-fat breakfast meal, at Hour 0 on Day 1 (test)

Treatment C: 133.3 mg/kg dose of MT1621, at Hour 0 on Day 1, following an overnight fast (reference) Parameters were ln-transformed prior to analysis.

Geometric least-squares means (LSMs) are calculated by exponentiating the LSMs from the ANOVA.

Geometric Mean Ratio (GMR) = 100*(test/reference)

Intra-subject CV % was calculated as 100*square root(exp[MSE] − 1), where MSE = residual variance from ANOVA.

Pharmacokinetic results from this study indicated that MT1621 was absorbed into the systemic circulation; more specifically, maximal dC and dT plasma concentrations (Cmax) were achieved at a median of 1.0 to 1.25 hours (Tmax) and 1.0 hour (Tmax) under fasted conditions and 1.0 and 3.0 under fed conditions. The geometric mean elimination half-life values for dC were 2.16 hours, 1.44 hours, and 3.01 hours at the 43.3 mg/kg, 86.7 mg/kg, and 133.3 mg/kg dose levels, respectively. The PK variability was high, >30% for both dC and dT. The baseline-corrected dC Cmax increased in a less than dose-proportional manner across the 3 fasted dose levels. Total extent of exposure (as measured by AUC0-t and AUC0-inf) for dC increased in a less than dose-proportional manner.

Plasma exposure to dC and dT following MT1621 were consistently higher at all 3 dose levels compared to endogenous (baseline) concentrations. The study demonstrates significantly increased systemic exposures of dC and dT after a single dose of MT1621.

Administration of 133.3 mg/kg MT1621 under fed conditions increased baseline adjusted Cmax and AUC by 79% and 137%, respectively, for plasma dC, and by 27% and 74%, respectively, for plasma dT compared to under fasted conditions, indicating a significant food effect on MT1621.

Dose-proportionality analysis of plasma dC indicated that while AUC appeared dose proportional (95% CI of slope [b] contained 1), Cmax was not. Dose-proportionality analysis of plasma dT results indicated that neither AUC nor Cmax was dose proportional.

Example 2. Open-Label Safety and Efficacy Study of MT1621 in Study Participants with TK2 Deficiency A phase 2 study was conducted as an open-label continuation of treatment with MT1621 in participants with TK2designed to evaluate the safety, tolerability, and PK of MT1621 (fixed dose combination of dC and dT supplied in a single packet). The study enrolled forty-seven (47) participants. After enrollment, participants transitioned from their current chemical grade 2'-deoxycytidine monophosphate/2'-deoxythymidine monophosphate (dCMP/dTMP) to deoxycytidine and deoxythymidine, or continued the use of deoxycytidine and deoxythymidine. Upon enrollment, participants who were on a stable maintenance dose of 400 mg/kg/day were treated with the same dose of deoxycytidine and deoxythymidine three-times daily (TID). Study participants who were on a total dose <400 mg/kg/day were transitioned to either 260 mg/kg/day (130 mg/kg/day of deoxycytidine and 130 mg/kg/day of deoxythymidine) TID, 520 mg/kg/day (260 mg/kg/day of deoxycytidine and 260 mg/kg/day of deoxythymidine) TID, or 800 mg/kg/day (400 mg/kg/day of deoxycytidine and 400 mg/kg/day of deoxythymidine) TID, depending on which was closest to the participants' previous dose.

Summary statistics of the key covariates of participants at baseline:

- Age (years); N=47; Mean (SD)=18.4 (18.7); Median (Min, Max)=9.90 (0.90, 75.6);
- Weight (kg): N=47; Mean (SD)=37.0 (22.6); Median (Min, Max)=31.5 (6.00, 99.5);
- Absolute eGFR (mL/min): N=46; Mean (SD)=285 (124); Median (Min, Max)=248 (111, 606);
- Creatinine Clearance (mL/min): N=47; Mean (SD)=203 (120); Median (Min, Max)=173 (42.9, 561);
- Sex: Male=27 (57.4%); Female=20 (42.6%); and
- Ethnicity: Unknown=0 (0%); Hispanic or Latino=14 (29.8%); Not Hispanic or Latino=33 (70.2%).

The early protocol for deoxycytidine and deoxythymidine administration was for the participants to take the drug product without regard to food. Moreover, the study did not carefully record food status of the participants when they took their daily doses and on the day of PK sampling. Later in the program, when an unexpected effect of food on PK was noted, the protocol was amended to instruct the participants to take the drug product with food. By then, planned PK samples had been taken in a majority of the participants. A total of 3 blood samples were collected from each individual following study Day 1 to measure dC plasma concentrations. Sparse PK blood sampling and PD endpoint collection was conducted according to the following schedule: at Month 1 sampled 0.5, 1, 2, or 3 hours post-dose; and at Month 3 sampled 8, 10, 12, or 14 hours post-dose. During sampling, it was noted whether food was consumed from 1 hour pre-dose to 2 hours post-dose. And, the lower limit of quantification (LLOQ) was 0.5 ng/mL for both dC and dT.

For the calculation of the PK parameters, raw (unadjusted) plasma dC and dT concentrations below the limit of quantitation (BLQ) were set to 1% the limit of quantitation (LOQ) of the assay. The plasma concentrations in participants could not be adjusted for baseline because the study did not sample pre-dose plasma. Since all participants had measurable pre-dose concentrations, Kel and associated PK parameters were not calculated for unadjusted data.

Analysis of the PK data pooled from five (5) studies (including those described in Examples 1 and 2) comprising three (3) Phase 1 studies in healthy volunteers (HV) and two (2) open-label Phase 2 studies that included both adult and pediatric study participants with TK2d. A total of 119 study participants were included, which consisted of 44 healthy study participants, 16 study participants with renal impairment (moderate or severe), and 59 participants with TK2d that included participants aged from 0.9 years to 75.6 year of age.

Pooled population PK analysis confirmed that the fed state was a statistically significant covariate of the PK of dC including the TK2 deficient participants. Table 6 reflects analysis of all dC PK data including those for TK2 deficient participants. The strength of the positive effect of food on the oral bioavailability of dC was 1.44, or an increase of 144%. This is the pertinent value to estimate food effect on dC exposures. It indicates that a fed state in general was associated with increased bioavailability of dC including for TK2 deficient participants. The decrease in the rate of dC absorption with food (parameter Ka in Table 6) is believed to be due to slower gastric/intestinal motility in the fed state. It is likely that the effect of food on dT concentration in participants with TK2 deficiency was masked by the high variability and limited PK sampling.

TABLE 6

Population Parameter Estimates and Bootstrap Results for the dC Final Pharmacokinetic Model

| Parameter (Units) | Description | NONMEM Estimate (% RSE) | Bootstrap Median[C] [2.5th-97.5th percentile] |
|---|---|---|---|
| dC BSL (ng/mL) | dC endogenous baseline level | 3.45 (3.29%) | 3.45 (3.21, 3.65) |
| Ka ($h^{-1}$) | Absorption rate constant | 0.466 (11.5%) | 0.465 (0.361, 0.638) |
| Food Effect on Ka[a] | | −0.441 (14.1%) | −0.438 (−0.549, −0.260) |
| F | Relative bioavailability | 1 (FIXED) | NA |
| Food Effect on F[b] | | 1.44 (16.3%) | 1.40 (1.01, 1.89) |
| CL/F (L/h) | Apparent clearance | 392000 (11.0%) | 392000 (318000, 492000) |
| V/F (L) | Apparent volume of distribution | 284000 (19.9%) | 278000 (193000, 461000) |
| IIV on BSL (CV %) [shrinkage] | | 27.3% (15.0%) [12.4%] | 26.9% (19.4%, 35.3%) |
| IIV on Ka (CV %) [shrinkage] | | 65.9% (13.6%) [23.9%] | 62.6% (36.1%, 81.8%) |
| IIV on F (CV %) [shrinkage] | | 75.1% (19.8%) [26.0%] | 73.3% (37.8%, 102%) |
| IIV on CL/F (CV%) [shrinkage] | | 61.6% (18.0%) [35.1%] | 60.3% (36.2%, 82.3%) |
| IIV on V/F (CV %) [shrinkage] | | 77.3% (18.0%) [44.5%] | 77.9% (39.3%, 107%) |

TABLE 6-continued

| Population Parameter Estimates and Bootstrap Results for the dC Final Pharmacokinetic Model | | | |
|---|---|---|---|
| Parameter (Units) | Description | NONMEM Estimate (% RSE) | Bootstrap Median[C] [2.5th-97.5th percentile] |
| IOV on F (CV %) | | 31.5% (8.01%) | 31.4% (26.3%, 37.9%) |
| Proportional RUV (%) | | 17.5% (3.76%) | 17.4% (16.1%, 18.8%) |

BSL = baseline;
Ka = absorption rate constant;
F = relative bioavailability;
CL/F = apparent oral clearance;
V/F = apparent oral volume of distribution;
RUV = residual unexplained variability
IIV = inter-individual variability;
IOV = inter-occasion variability;
%RSE = relative standard error expressed as a percent, calculated as (standard error)/(estimate)*100;
IIV and IOV are expressed as CV %, calculated as sqrt($\omega^2$)*100.
Clearance and volume terms were allometrically scaled using fixed exponents of 0.75 and 1, respectively, with body weight centered on 70 kg.
[a]$Ka_{Fed}$ = Ka*(1 + Food effect on Ka)
[b]$F_{Fed}$ = F*(1 + Food effect on F)
[c]summary from 734 out of 1000 bootstraps that minimized successfully.

The dC PK was described by a one-compartment model with a first-order absorption and a first order elimination and found that:

- Endogenous dC baseline was the same across studies and populations;
- Body weight was found to be positively correlated with apparent oral clearance (CL/F) and apparent oral volume of distribution (V/F), using fixed allometric exponents of 0.75 and 1, respectively;
- Age was not determined to be a covariate of significance;
- Relative bioavailability (F) increased by ~150% with food intake (standard or high-fat meal);
- Absorption rate constant (Ka) decreased by ~44% with food intake (standard or high-fat meal);
- Latino/Hispanic ethnicity was not determined to be a covariate of significance; and
- No difference in F was detected between HV and TK2 deficient participants.

The dT PK was described by a one-compartment model with 2 parallel first-order absorptions with lag times and first-order elimination and found that:

- Endogenous dT baseline was different across studies (ranging from 0.220 to 1.14 ng/mL);
- Body weight was not found to be a significant covariate on CL/F nor V/F;
- Age was not determined to be a covariate of significance;
- About 83% of relative bioavailability (F) was ascribed to the first depot compartment;
- F was increased by ~120% with a high-fat content meal;
- F was lower by a factor of ~0.4 at dose 43.3 mg/kg and a factor of ~0.7 at dose 86.6 mg/kg relative to the F value of dose 133.3 mg/kg in healthy study participants; separate analysis of Phase 1 studies in HV had previously shown that exposures to dT following single ascending doses in this dose range increased in a more than dose proportional manner;
- Absorption rate constant from first input compartment (K12) and lag time from second input compartment (ALAG3) both decreased with high-fat content meal by ~80%;
- F decreased in Latino/Hispanic population by ~50%; and
- F was lower in healthy volunteers compared to TK2 deficient participants (70% to 90%).

The dC model was able to describe the PK of dC with good precision and with limited or no bias. The population PK model provided a robust fit to the observed data with stable PK parameter estimates associated with high precision. The dC model was deemed suitable to describe dC exposure in patients with TK2d for further pharmacokinetic/pharmacodynamic or exposure-response analyses.

The dT model was able to reasonably describe the PK of dT in HV, study participants with renal impairment, and in participants with TK2d with good precision and limited bias. However, high residual unexplained variability in the model signals that while it might be suitable for the current dataset, predictive utility of the model is limited. The dT exposure in TK2 deficient participants derived from the model should, therefore, be interpreted with caution.

In conclusion, PK changes induced by a standardized high-fat, high-calorie meal reflect the greatest effects on gastrointestinal physiology. The resulting maximum effects on the oral bioavailability on a drug are generalizable to all subjects including healthy and those with TK2 deficiency. Regulations prescribe that the effect of food on drug PK be evaluated with a standardized high-fat meal preferably in healthy adult participants of an adequate sample size under controlled conditions with dense/rich PK sampling. To our knowledge, there is no physiological basis to expect that the underlying disease (TK2 deficiency) would cause differential effects of food on the bioavailability of dC and dT compared to healthy subjects. Therefore, results from the dedicated studies on healthy subjects (Example 1) provide definitive and reliable findings on the effect of food on oral PK of dC and dT which are fully applicable to the target patient population. The ability of the population PK model to independently identify food (for dC in healthy and TK2 deficient participants) and the high-fat meal (for dT, in healthy participants) as a significant covariate of PK provides additional support.

What is claimed is:

1. A method of increasing the oral bioavailability of deoxycytidine (dC) and deoxythymidine (dT) to a patient receiving therapy for a mitochondrial depletion syndrome (MDS) comprising administering to the patient in need thereof, or instructing a patient caregiver to administer, a therapeutically effective amount of dC and dT with food, wherein the dC and dT is administered at the same time as or up to about 30 minutes after oral administration of food, and wherein the food is a high fat, high calorie meal.

2. The method of claim 1, wherein the therapeutically effective amount of a combined weight of dC and dT is between about 200 mg/kg/day and about 800 mg/kg/day.

3. The method of claim 1, wherein the therapeutically effective amount of a combined weight of dC and dT is 800 mg/kg/day.

4. The method of claim 1, wherein the dC and dT is administered as a fixed dose combination pharmaceutical composition.

5. The method of claim 1, wherein the dC and dT is administered after combining two pharmaceutical compositions in equal parts by weight, one comprising dC and one comprising dT.

6. The method of claim 1, wherein the rate of absorption of dC and dT is increased.

7. The method of claim 1, wherein the extent of the absorption of dC and dT is increased.

8. The method of claim 1, wherein the circulating half-life of dC and dT is increased.

9. The method of claim 1, wherein the dC and dT doses are administered from one time to three times daily and one or more of the doses are administered with food.

10. The method of claim 1, wherein the mean maximum plasma concentration (Cmax) and the area under the plasma concentration time curve ($AUC_{0-t}$) of deoxycytidine and deoxythymidine in the subject in need thereof is increased when dC and dT are administered with food, compared to when dC and dT are administered under fasting conditions.

11. The method of claim 10, wherein Cmax of dC increases by at least about 79%.

12. The method of claim 10, wherein $AUC_{0-t}$ of dC increases by at least about 137%.

13. The method of claim 10, wherein Cmax of dT increases by at least about 27%.

14. The method of claim 10, wherein $AUC_{0-t}$ of dT increases by at least about 74%.

15. The method of claim 1, wherein the MDS is TK2 deficiency disorder or POLG deficiency disorder.

16. The method of claim 1, wherein the dC and dT is in the form of a composition and is provided with a container containing printed labeling advising that administration with food results in an increase in the maximal plasma concentration (Cmax) and extent of absorption (AUC (last)) compared to administration without food and that the composition should be taken with food.

17. A method of increasing the amount of deoxycytidine (dC) absorbed by a patient's body comprising administering a dose with a combined weight of dC and deoxythymidine (dT) of between about 100 mg/kg and about 200 mg/kg containing equal parts of dC and dT, wherein the administering is with food, wherein the dC and dT is administered at the same time as or up to about 30 minutes after oral administration of food, and wherein the food is a high fat, high calorie meal.

18. The method of claim 17, wherein the dose with a combined weight of dC and dT of between about 100 mg/kg and about 200 mg/kg is administered three times a day.

19. The method of claim 17, wherein the patient has a mitochondrial depletion syndrome (MDS).

20. A method of treating a mitochondrial depletion syndrome patient comprising, administering to the patient a therapeutically effective amount of deoxycytidine (dC) and a therapeutically effective amount of deoxythymidine (dT) and directing the patient to take the dC and dT with food, wherein the dC and dT is administered at the same time as or up to about 30 minutes after oral administration of food, and wherein the food is a high fat, high calorie meal.

21. The method of claim 20, wherein the administration to the patient is substantially at the same time as consumption of the food.

22. The method of claim 21, wherein the dC and dT is in the form of a powder composition for reconstitution in water or juice.

23. The method of claim 22, wherein the powder is in the form of a fixed dose combination pharmaceutical composition of dC and dT.

* * * * *